(12) United States Patent
Auerbach et al.

(10) Patent No.: US 9,381,531 B2
(45) Date of Patent: Jul. 5, 2016

(54) LIQUID DISPENSER

(75) Inventors: Judith Auerbach, Niederteufen (CH);
Juergen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 14/343,262

(22) PCT Filed: Jul. 30, 2012

(86) PCT No.: PCT/EP2012/064899
§ 371 (c)(1),
(2), (4) Date: Mar. 6, 2014

(87) PCT Pub. No.: WO2013/034365
PCT Pub. Date: Mar. 14, 2013

(65) Prior Publication Data
US 2014/0224841 A1    Aug. 14, 2014

(30) Foreign Application Priority Data

Sep. 9, 2011    (DE) .......................... 10 2011 082 420

(51) Int. Cl.
| | |
|---|---|
| *B65D 88/54* | (2006.01) |
| *G01F 11/00* | (2006.01) |
| *B05B 11/00* | (2006.01) |
| *A61M 15/08* | (2006.01) |
| *G01F 11/02* | (2006.01) |
| *A61M 11/00* | (2006.01) |
| *B05B 1/34* | (2006.01) |

(52) U.S. Cl.
CPC .......... *B05B 11/3001* (2013.01); *A61M 11/007* (2014.02); *A61M 15/08* (2013.01);
(Continued)

(58) Field of Classification Search
CPC ............ B05B 11/3004; B05B 11/3016; B05B 11/3001; B05B 11/0067; B05B 1/3426; B05B 11/3047; B05B 11/3074; A61M 15/08; A61M 2202/0468; G01F 11/028
USPC ..................................................... 222/321.6
See application file for complete search history.

(56) References Cited

U.S. PATENT DOCUMENTS 6,053,368 A  *  4/2000  Geimer .................... 222/189.09
7,798,375 B2     9/2010  Le Maner
(Continued)

FOREIGN PATENT DOCUMENTS

| EP | 1 768 789 B1 | 1/2008 |
|---|---|---|
| FR | 2 862 107 A1 | 5/2005 |
| JP | 62-139971 U | 9/1987 |
| WO | WO 2005/048875 A2 | 6/2005 |
| WO | WO 2006/042641 A1 | 4/2006 |
| WO | WO 2010/004224 A2 | 1/2010 |

OTHER PUBLICATIONS

International Search Report issued in International Application No. PCT/EP2012/064899 including English translation, date of mailing Oct. 9, 2012 (4 pages).

*Primary Examiner* — Patrick M Buechner
*Assistant Examiner* — Jeremy W Carroll
(74) *Attorney, Agent, or Firm* — Flynn, Thiel, Boutell & Tanis, P.C.

(57) ABSTRACT

Liquid dispensers with a housing, a reservoir for receiving liquid prior to discharge, a discharge opening, and a conveyor device for conveying liquid from the reservoir to the discharge opening.

The conveyor device includes a metering chamber with a cylindrical wall, and a piston adapted to the cylindrical wall to allow a sliding movement thereon. The metering chamber and the piston displaced relative to each other between starting and end positions. An outlet side of the metering chamber is adjoined by an outlet chamber, and an inlet side of the metering chamber is adjoined by an inlet chamber. The piston is arranged in the inlet chamber when in the starting position and in the outlet chamber when in the end position. During the transition from the starting position to the end position, the liquid in the metering chamber is pressurized for discharge through the discharge opening.

20 Claims, 2 Drawing Sheets

(52) U.S. Cl.
CPC ......... *B05B11/0067* (2013.01); *B05B 11/3004* (2013.01); *G01F 11/028* (2013.01); *A61M 2202/0468* (2013.01); *B05B 1/3426* (2013.01); *B05B 11/3047* (2013.01); *B05B 11/3074* (2013.01)

(56) References Cited

U.S. PATENT DOCUMENTS

| | | | |
|---|---|---|---|
| 7,946,455 | B2 | 5/2011 | Ritsche et al. |
| 8,016,165 | B2 | 9/2011 | Margheritis et al. |
| 2003/0019493 | A1 | 1/2003 | Narayan et al. |
| 2003/0057297 | A1 | 3/2003 | Py |
| 2006/0011659 | A1* | 1/2006 | Greiner-Perth et al. ... 222/321.7 |
| 2006/0016833 | A1* | 1/2006 | Greiner-Perth ............ 222/383.1 |
| 2007/0272712 | A1* | 11/2007 | Pardonge et al. .......... 222/321.6 |
| 2007/0272713 | A1* | 11/2007 | Le Maner .................. 222/321.6 |
| 2008/0029544 | A1* | 2/2008 | Margheritis et al. ..... 222/153.13 |
| 2008/0035223 | A1 | 2/2008 | Ritsche et al. |
| 2009/0255959 | A1* | 10/2009 | Pruvot ....................... 222/321.6 |
| 2011/0114676 | A1* | 5/2011 | Margheritis et al. .......... 222/391 |

* cited by examiner

LIQUID DISPENSER

FIELD OF USE AND PRIOR ART

The invention relates to a liquid dispenser, in particular for pharmaceutical liquids, with a housing, a liquid reservoir for receiving the liquid prior to the discharge, a discharge opening, and a manually actuatable conveyor device for conveying liquid from the liquid reservoir to the discharge opening. The invention also relates to a discharge head for such a dispenser.

Liquid dispensers of the type in question are generally known from the prior art. Thus, for example, EP 1 768 789 B1 and WO 2010/004224 A2 describe dispensers of the type in question. Such dispensers of the type in question are used to discharge liquids, for example pharmaceutical or cosmetic liquids. They are designed as portable units that can be easily carried around by a patient and user.

WO 2006/042641 A1 discloses a liquid dispenser whose metering volume is defined via a sliding valve, which is surrounded by an annular metering chamber. The sliding valve itself does not serve directly to pressurize the liquid, and instead, during the actuation, it merely temporarily closes the liquid path between the metering chamber and a liquid reservoir, in order thereby to indirectly control the increase in pressure in the metering chamber and the discharge of the liquid from the latter.

Particularly in dispensers of the kind that are used to discharge pharmaceutical liquids, a high degree of precision as regards the amount of liquid discharged is sometimes important depending on the specific application purpose. At the same time, dispensers of the type in question, which are usually designed not to be reused, must be able to be produced at reasonable cost.

PROBLEM AND SOLUTION

The problem addressed by the invention is to make available a dispenser of the type in question which affords a high degree of metering precision. In particular, this dispenser should also be able to be produced and assembled at reasonable cost.

For this purpose, according to the invention, a dispenser of the type in question is proposed which has a special conveyor device. This conveyor device comprises a metering chamber with a cylindrical wall, and a piston that is adapted, in terms of the cross section, to the cylindrical wall of the metering chamber so as to allow a sliding movement thereon. At one end, the metering chamber has an outlet side via which it is connected to the discharge opening of the dispenser. Lying opposite the outlet side, it also has an inlet side via which it is connected to the liquid reservoir. At the inlet side, the metering chamber is adjoined by an inlet chamber. Likewise, the outlet side of the metering chamber is adjoined by an outlet chamber. The cross section of the inlet chamber and of the outlet chamber is in each case larger than the cross section of the piston. Provision is also made that the piston is arranged in the inlet chamber when in a starting position of an actuation of the conveyor device and is arranged in the outlet chamber when in an end position of the actuation, and, during the transition from the starting position to the end position, the piston passes through the metering chamber and, in so doing, the liquid in the metering chamber is pressurized for the purpose of discharging liquid through the discharge opening.

The conveyor device of a liquid dispenser of the type in question thus has said cylindrical metering chamber through which, in the course of an actuation of the dispenser, the piston passes while bearing on the walls of the metering chamber. While the piston is located in the metering chamber and thus bears on the cylindrical wall of the metering chamber, it forces the liquid, previously located in the metering chamber, in the direction of the outlet side of the metering chamber and thus in the direction of the discharge opening.

A high degree of precision in the discharge is achieved by the widening of the metering chamber at the inlet side thereof and also at the outlet side thereof. This is due to the fact that, during the actuation of the conveyor device, discharge does not take place as long as the piston is still arranged in the inlet chamber and thus does not yet tightly close the metering chamber at the inlet side thereof, and that the pressure built up in the liquid during the actuation drops directly at the moment when the piston, at the outlet side of the metering chamber, loses contact with the wall of the metering chamber. The partial distance of the movement of the piston relative to the metering chamber from the starting position to the end position, used for the discharge of the liquid, is accordingly the distance between a first relative position, in which the piston comes into contact for the first time with the wall of the metering chamber, and a second relative position, in which this contact is again lost.

The linear relationship between this distance, effective for the discharge, and the amount of liquid discharged permits a particularly simple adaptation of the metering volume of a liquid dispenser. For the purpose of this adaptation, all that is needed is to change the length of the metering chamber, which generally requires adapting only the component part that forms the wall of the metering chamber, while all the other component parts of the liquid dispenser can remain identical for different desired metering volumes.

By virtue of the fact that, in the design according to the invention, it is the piston passing through the metering chamber widened at both ends that serves to pressurize the liquid, a very narrow structure of the dispenser according to the invention is made possible by comparison with the above-mentioned WO 2006/042641 A1.

The liquid dispenser preferably has two housing portions movable relative to each other and directly maneuverable by a user, wherein the metering chamber is provided in a fixed position on a first of the housing portions, and wherein the piston is provided in a fixed position on a second of the housing portions. Thus, the movement of the housing portions that is brought about manually from the outside also corresponds to the movement of the piston relative to the metering chamber. It is possible to do without complicated mechanical couplings between the movement of the piston and of the metering chamber, on the one hand, and the movement of the housing portions accessible from the outside, on the other hand.

It is particularly preferable if the liquid reservoir is connected to the conveyor device via two different liquid paths. A first of these liquid paths leads from the liquid reservoir, past the piston on the outside and into the inlet chamber or the outlet chamber. During an actuation of the conveyor device, this first liquid path is the liquid path which is closed when the piston enters the metering chamber and which is opened when the piston emerges again at the opposite end from the metering chamber. In this liquid path, there is preferably no valve provided between the liquid reservoir and the piston, such that, whenever the piston leaves the metering chamber at the outlet side, the pressure in the liquid dispenser is equalized all the way to the liquid reservoir.

It is preferable if a second liquid path is provided which leads from the liquid reservoir, through the piston and into the metering chamber, wherein an inlet valve that closes when there is an overpressure in the metering chamber is provided in this liquid path. Therefore, this second liquid path does not run past the piston, but instead through the piston. Since this second liquid path is therefore not directly closed by the entry of the piston into the metering chamber, it has a nonreturn valve which closes when the liquid in the metering chamber is pressurized. During a return stroke, in which the piston and the metering chamber are moved mutually in the direction of their starting position, this second liquid path has the effect that new liquid can already be sucked from the liquid reservoir into the metering chamber while the piston is still arranged in the metering chamber.

It is also conceivable in principle to omit this second liquid path, such that the return stroke is associated with the development of a strong underpressure in the metering chamber until the piston has reached the inlet chamber and liquid can be sucked in. However, the force needed for the return stroke is greatly reduced by the second liquid path, which means, among other things, that a weaker restoring spring can be used.

To make it easier for the piston to enter the metering chamber, provision is preferably made that a circumferential bevel is provided in a transition area between the inlet chamber and the metering chamber. This bevel preferably encloses an angle of between 15° and 45° with the actuation direction. By means of a bevel being provided here, it is possible to counter the development of damage to the piston or to the piston lip of the latter. To make it easier for the piston to enter the metering chamber, it is also possible for the widening of the inlet chamber and/or of the outlet chamber to be obtained in such a way that widening is provided only in partial areas of the circumference. This could be achieved, for example, by elongate grooves which are provided in the wall of the inlet chamber or outlet chamber, which wall otherwise has the same internal diameter as the metering chamber.

In a particularly preferred embodiment, the metering chamber is provided in a fixed position on a housing portion of the housing, wherein this housing portion has at least two component parts connected to each other in a fixed position, of which an outer component part is accessible from the outside, and of which an inner component part has the metering chamber. The two-part design of the housing portion having the metering chamber results in a very simple modular adaptability of the dispenser to different application purposes and in particular to different desired metering volumes. Thus, the preferably sleeve-shaped outer component part, which is designed to receive the preferably likewise approximately sleeve-shaped inner component part, can remain unchanged when the inner component part is adapted in terms of the length of its metering chamber in order to achieve a modified metering volume. The result of this is a smaller number of parts and, therefore, reduced production costs.

A liquid dispenser according to the invention preferably has a restoring spring, which is arranged between its two housing portions and applies a force to the housing portions in the direction of the starting position. In a particularly preferred embodiment, this restoring spring is arranged in such a way that it presses the inner component part permanently against the outer component part. The opposite end of the restoring spring is usually supported on the other housing portion having the piston provided thereon. As a result of the permanent force of the inner component part against the outer component part, it is possible to omit an additional and costly coupling mechanism between the two component parts. The mobility of the outer component part relative to the other housing portion having the piston arranged thereon is preferably limited by suitable stops, which therefore also act against separability.

It is particularly advantageous if the discharge opening is assigned an outlet valve that opens in a pressure-dependent manner. This outlet valve ensures a minimum pressure of the liquid at the time of discharge, for example in order to generate a spray jet. It also ensures that no medium can escape before the piston enters the metering chamber, since the low overpressure, which is brought about by the movement of the piston in the inlet chamber before entering the metering chamber, is not sufficient to open the outlet valve. The valve additionally has the effect that the discharge opening is closed during the return stroke, such that no air can be sucked through this opening into the dispenser.

For a particularly simple design, it is also advantageous if a one-piece component is provided on the dispenser, which component is intended, on the one hand, to be secured on an outlet nozzle of a liquid reservoir shaped like a bottle and on which, on the other hand, the piston is provided.

Furthermore, the invention also relates to a discharge head for a dispenser of the type described above. The advantages and possible variations that have been discussed above in connection with the dispenser also apply equally to such a discharge head according to the invention.

BRIEF DESCRIPTION OF THE DRAWINGS

Further aspects and advantages of the invention will become clear not only from the claims but also from the following description of a preferred illustrative embodiment of the invention, which embodiment is explained below with reference to the figures, in which:

DETAILED DESCRIPTION OF THE ILLUSTRATIVE EMBODIMENT

Figure 1:
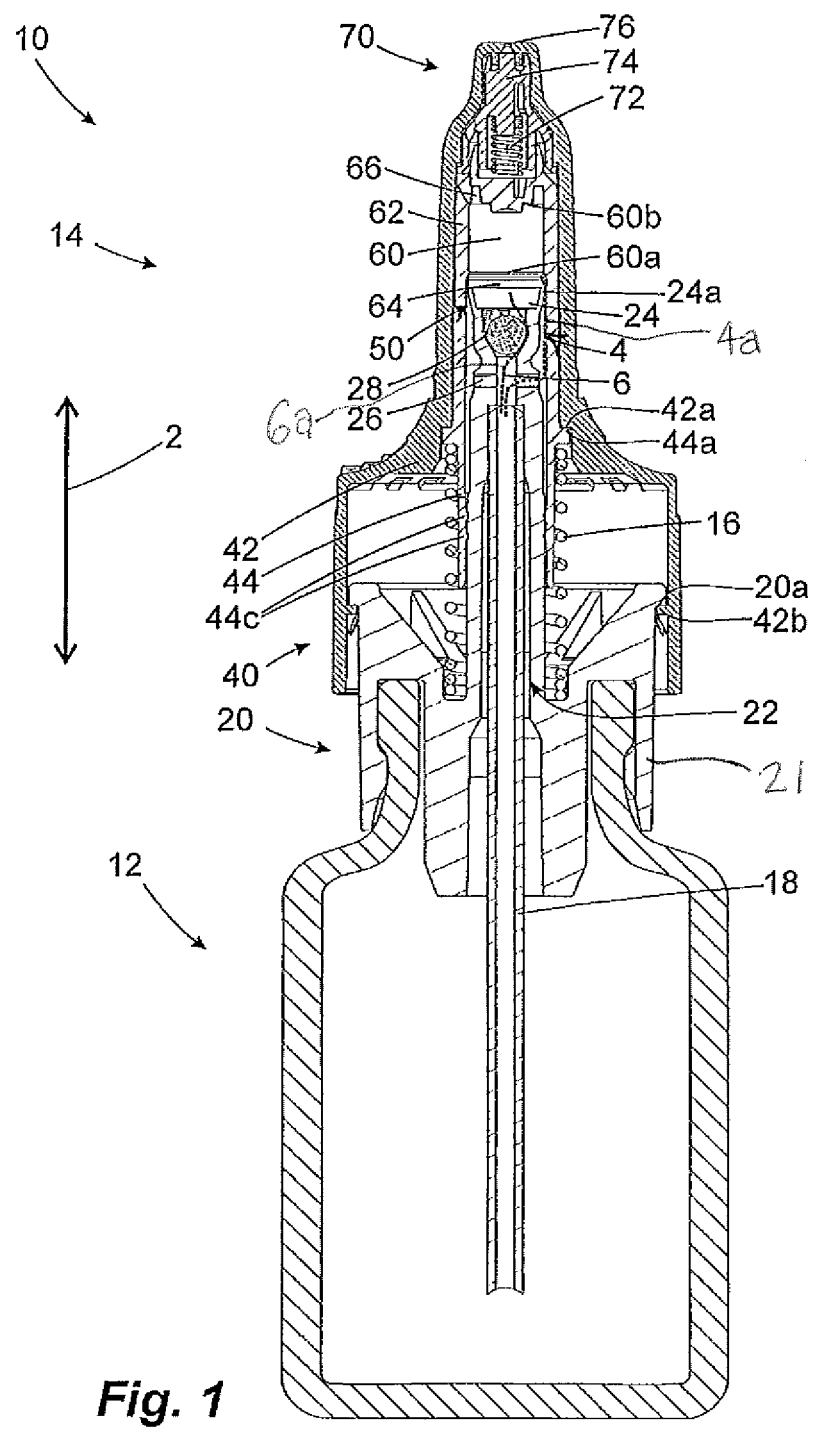
FIG. 1 shows an overall view of a liquid dispenser according to the invention.

FIG. 1 shows a dispenser according to the invention with a bottle-like liquid reservoir 12 and a discharge head 14 mounted on the latter. The main parts of the discharge head 14 are a first housing portion 20, which is provided with a coupling portion 21 for fitting on the liquid reservoir 12, and a second housing portion 40, which is movable relative to the first housing portion 20 in the sense of an actuation direction 2. Between the housing portions 20, 40, a restoring spring 16 is provided which permanently forces the second housing portion 40 in the direction of its upper end position shown in FIG. 1.

The first housing portion 20 and the second housing portion 40 together form a conveyor device 50 of the kind described below. The one-piece housing portion 20 has a centrally disposed and upwardly extending extension piece 22 which is designed in the manner of a hollow pipe and which, at its upper end, merges into a piston 24 having a peripheral piston lip 24a. Inside this extension piece 22, a dip tube 18 is provided through which liquid can pass from the liquid reservoir 12 to the upper end of the extension piece 22. There, the liquid can emerge laterally from the extension piece 22 along a first liquid path 4 through radial channels 26 and along a portion 4a of the first liquid path 4 which extends exteriorly of the piston 24. However, it can also emerge forward from the extension piece 22 through an inlet valve 28, designed as a nonreturn valve, along a second liquid path 6 inside the piston lip 24a. This second liquid path 6 has a portion 6a which extends interiorly through the piston 24.

The extension piece 22 extends into the second housing portion 40, which in particular has an outer component part 42 and an inner component part 44. The inner component part 44 is designed like a tube or like a sleeve and is fitted into the sleeve-shaped outer component part 42. The relative position is defined by corresponding stops 44a, 42a on the two component parts 42, 44. There is no need for the inner component part 44 to be secured in any special way in the outer component part 42, since the inner component part 44 is permanently pressed against the outer component part 42 by the restoring spring 16. The outer component part 42 is in turn limited, in terms of its mobility relative to the first housing portion 20, by an inwardly facing retaining collar 42b on the first housing portion 20. Together with a cylindrical area of the extension piece 22, the inner component part 44 seals off liquid-conveying areas of the discharge head 14 of the dispenser from the environment and for this purpose has inwardly directed sealing rings 44c formed integrally on the lower end thereof.

For interaction with the piston 24, a metering chamber 60 is provided on the second housing portion 40, specifically on the inner component part 44 of the latter. This metering chamber 60 is defined by being surrounded by a peripheral wall 62, which is adapted to the piston 24 in such a way that, when the piston lip 24a bears on the wall 62 of the metering chamber, the liquid can no longer pass from the metering chamber 60 back along the first liquid path 4 in the direction of the liquid reservoir 12. The inlet side 60a of the metering chamber is adjoined by an inlet chamber 64 with a widened cross section 64a. The outlet side 60b of the metering chamber 60 is adjoined by an outlet chamber 66 with a widened cross section 66a.

In the arrangement of the piston 24, in particular of its piston lip 24a, both in the inlet chamber 64 and also in the outlet chamber 66, the piston lip 24a does not lie sealingly, at least at the periphery, on the inner wall of the inner component part 44. A complete separation of the pressure above the piston from the pressure in the liquid dispenser 12 is therefore only present when the piston 24 is located inside the metering chamber 60 and its piston lip 24a bears on the wall 62 of the metering chamber. By contrast, a communicating connection between all the liquid-conveying areas inside the dispenser is present both before the entry of the piston 24 into the metering chamber 60 from the inlet chamber 64 below the metering chamber 60 and also after the upward emergence of the piston 24 from the metering chamber 60 as the piston 24 enters the outlet chamber 66.

The far side of the outlet chamber 66 is adjoined by a pressure-dependent, opening outlet valve 70, which has a spring 72 by which a valve body 74 is pressed permanently against a discharge opening 76. Only when there is a sufficient overpressure can this valve body 74 be moved downward counter to the force of the spring 72, such that it frees the discharge opening 76 for the purpose of emergence of the liquid.

Figure 2C:
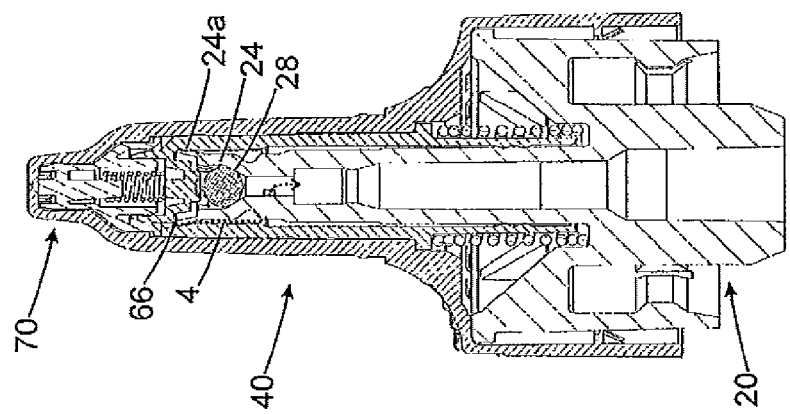
FIG. 2a to FIG. 2c show a discharge head of the liquid dispenser from FIG. 1 in three stages during actuation.
Figure 2B:
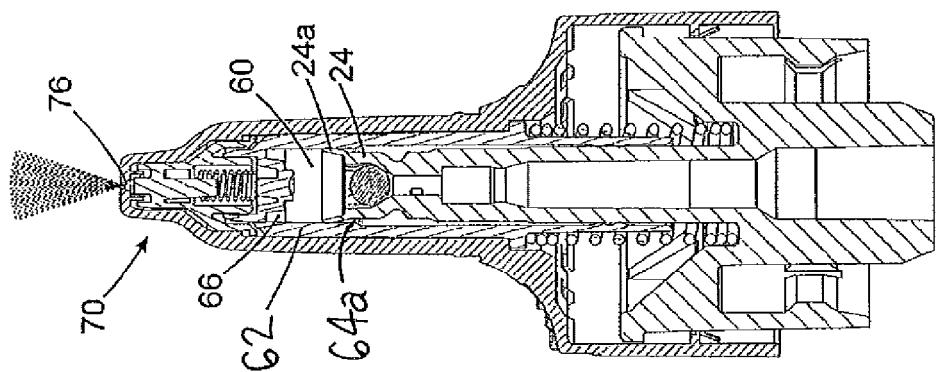
Figure 2A:
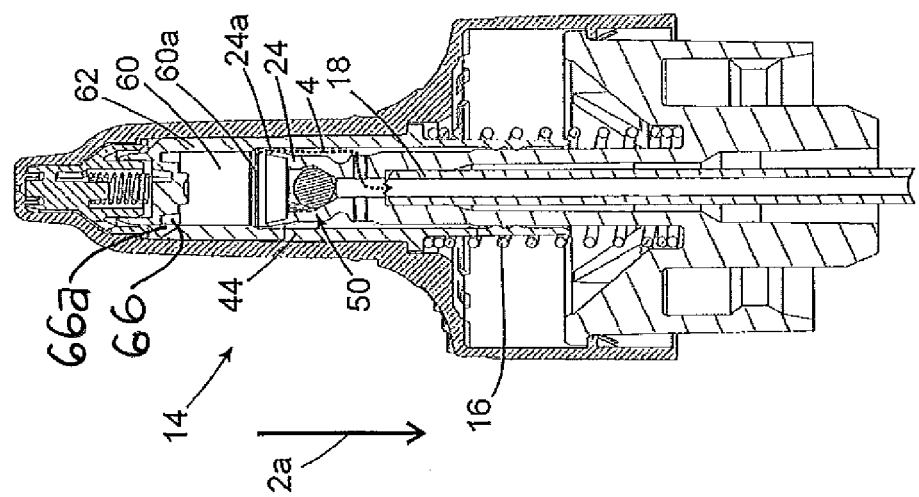

FIGS. 2a to 2c illustrate a discharge procedure using the liquid dispenser from FIG. 1. The dispenser is to be considered here as being already in an operational state. In other words, all the liquid-conveying spaces in the area of the conveyor device 50 are already filled with liquid as intended. The production of the operational state is discussed in detail below.

FIG. 2a shows the discharge head 14 of the dispenser from FIG. 1 in a starting position, in which the second housing portion 40 adopts its upper end position relative to the first housing portion 20 fixed on the liquid reservoir. Proceeding from this starting state, an actuation takes place in which the second housing portion 40 is pressed down in the direction of the arrow 2a counter to the force of the restoring spring 16. This downward pressing, which is associated with a displacement of the piston 24 relative to the inner component part 44, leads to a reduction of the liquid-conveying volume in the area of the conveyor device 50. Excess liquid from the conveyor device is forced along the first liquid path 4 back into the dip tube 18. This first phase of the actuation ends when the piston lip 24a of the piston emerges into the metering chamber 60 from the direction of the inlet side 60a. Here, the piston lip 24a bears on the wall 62 of the metering chamber and thus closes the first liquid path 4. The second liquid path 6 through the inlet valve 28 is likewise closed, at this moment at the latest, under the effect of the overpressure arising in the pressure chamber 60.

At the moment when the piston lip 24a comes to bear peripherally on the wall 62 of the metering chamber, a second phase of the actuation begins, which is illustrated by FIG. 2b. The continued pressing down of the second housing portion 40 leads to pressurization of the liquid in the metering chamber 60. Since this liquid can no longer escape in the direction of the liquid reservoir 12, the pressure that builds up causes the outlet valve 70 to open, such that the liquid from the metering chamber 60 and from other liquid-conveying areas can reach the outside through the discharge opening 76 in the area of the outlet valve 70.

The discharge procedure ends at the moment when the sealing lip 24a enters the outlet chamber 66. Here, the sealing lip 24a at least partially loses contact with the wall 62, such that the first liquid path 4 is opened again in the manner illustrated in FIG. 2c. The pressure in the outlet chamber 66 and in the liquid-conveying areas of the outlet valve 70 abruptly drops, such that the outlet valve 70 immediately closes, and any continuation of the relative movement between the housing portions 20, 40 merely causes an escape of the liquid from these areas into the dip tube 18.

During the subsequent return stroke, the piston 24 enters the metering chamber 60 again and in so doing once again closes the first liquid path 4. However, the underpressure arising in the metering chamber 60 during the return stroke causes the inlet valve 28 to open, with the result that, during the return stroke, liquid is sucked along the second flow path 6 from the liquid reservoir 12 into the metering chamber 60 via the dip tube 18. As soon as the return stroke is completed, and the state shown in FIG. 2a has therefore once again been reached, the dispenser is ready for a renewed discharge.

Before the dispenser 10 is put to use for the first time, the metering chamber 60, the inlet chamber 64, the outlet chamber 66 and the free spaces in the area of the valve 70 are still filled with air. The first two or three strokes result in this air being forced out. It is compressed in these so-called priming strokes to such an extent that the outlet valve 70 opens and allows the air to escape.

The dispenser shown, in particular the discharge head 14 shown, makes it possible, with a very simple structure and with a very small number of parts, to achieve a precise discharge of predefined amounts of liquid. The liquid to be discharged in the context of an actuation movement is defined only by the cylinder volume of the metering chamber 60. It is therefore very easy to adapt the dispenser to different metering volumes. In the present dispenser, it is sufficient for the inner component part 44 to be replaced by a slightly modified inner component part 44 whose metering chamber is changed by a shift of the transition area between the inlet chamber and the metering chamber. Adaptation of other component parts of the dispenser is unnecessary.

The invention claimed is:

1. A liquid dispenser for pharmaceutical liquids, comprising:
a housing;
a liquid reservoir for receiving the liquid prior to discharge of the liquid from the dispenser;
a discharge opening; and
a manually actuatable conveyor device for conveying liquid from the liquid reservoir to the discharge opening, the conveyor device comprising a metering chamber with a cylindrical wall, and a piston having a cross section dimensionally adapted to the cylindrical wall of the metering chamber so as to allow a sliding movement thereon, the metering chamber and the piston being manually displaceable relative to each other between a starting position and an end position, the metering chamber having an outlet side through which the metering chamber is connected to the discharge opening and an inlet side through which the metering chamber is connected to the liquid reservoir, the outlet side of the metering chamber being adjoined to an outlet chamber and the inlet side of the metering chamber being adjoined to an inlet chamber, a cross section of each of the inlet and outlet chambers being larger than the cross section of the piston, the piston being arranged in the inlet chamber when in the starting position and arranged in the outlet chamber when in the end position, and, during a transition from the starting position to the end position, the liquid in the metering chamber is pressurized to discharge liquid through the discharge opening, the liquid reservoir being connected to the conveyor device via two liquid paths, the two liquid paths including a first liquid path leading from the liquid reservoir, past the piston and into the inlet chamber or the outlet chamber, the first liquid path being closed when the piston enters the inlet side of the metering chamber from the inlet chamber and being open when the piston exits the outlet side of the metering chamber and enters the outlet chamber, and a second liquid path leading from the liquid reservoir, through the piston and into the metering chamber, the conveyor device further including an inlet valve disposed in the second liquid path, the inlet valve closing when there is an overpressure in the metering chamber.

2. The liquid dispenser as claimed in claim 1, wherein the housing has two housing portions movable relative to each other, wherein the metering chamber is provided in a fixed position in a first of the two housing portions, and the piston is provided in a fixed position on a second of the two housing portions.

3. The liquid dispenser as claimed in claim 1, wherein a bevel with an angle of between 15° and 45° in relation to an actuation direction of the dispenser is provided in a transition area between the inlet chamber and the inlet side of the metering chamber.

4. The liquid dispenser as claimed in claim 1, wherein the metering chamber is provided in a fixed position on a housing portion of the housing, the housing portion having at least two component parts connected to each other in a fixed position, the two component parts including an outer component part accessible from the outside, and an inner component part defining the metering chamber.

5. The liquid dispenser as claimed in claim 4, wherein the housing portion is a first housing portion and the housing includes a second housing portion movable relative to the first housing portion, the liquid dispenser further including a restoring spring disposed to bias the first and second housing portions in the starting position, wherein the inner component part is pressed against the outer component part by the restoring spring.

6. The liquid dispenser as claimed in claim 1, further including an outlet valve disposed adjacent the discharge opening, the outlet valve opening in a pressure-dependent manner to allow discharge of liquid through the discharge opening.

7. The liquid dispenser as claimed in claim 1, wherein the liquid reservoir is bottle-shaped and includes an outlet nozzle, the housing including a component part secured on the outlet nozzle, the component including the piston.

8. The liquid dispenser as claimed in claim 1, wherein the first liquid path is disposed to provide fluid communication between the liquid reservoir and either the inlet chamber or the outlet chamber via a first liquid path portion which extends exteriorly of the piston, and the second liquid path is disposed to provide fluid communication between the liquid reservoir and the metering chamber via a second liquid path portion which extends interiorly through the piston.

9. The liquid dispenser as claimed in claim 8, wherein the cylindrical wall defines both of the inlet chamber and the outlet chamber and the metering chamber is disposed between the inlet chamber and the outlet chamber, the inlet and outlet chambers each have a cross section which is larger than a cross section of the metering chamber, an exterior of the piston makes sealing contact with the cylindrical wall and closes the first liquid path when the piston is disposed in the metering chamber, and the piston is not in sealing contact with the cylindrical wall and the first liquid path is open when the piston is disposed in the inlet and outlet chambers.

10. A discharge head for a liquid dispenser, comprising:
a housing having a coupling portion for mounting on a liquid reservoir;
a discharge opening; and
a manually actuatable conveyor device for conveying liquid from the coupling portion to the discharge opening, the conveyor device comprising a metering chamber with a cylindrical wall, and a piston having a cross section dimensionally adapted to the cylindrical wall of the metering chamber so as to allow a sliding movement thereon, the metering chamber and the piston being manually displaceable relative to each other between a starting position and an end position, the metering chamber having an outlet side through which the metering chamber is connected to the discharge opening and an inlet side through which the metering chamber is connected to the coupling portion, the outlet side of the metering chamber being adjoined to an outlet chamber and the inlet side of the metering chamber being adjoined to an inlet chamber, a cross section of the outlet and inlet chambers being larger than the cross section of the piston, the piston being arranged in the inlet chamber when in the starting position and arranged in the outlet chamber when in the end position, and, during a transition from the starting position to the end position, the liquid in the metering chamber is pressurized to discharge liquid through the discharge opening, the coupling portion being connected to the conveyor device via two liquid paths, the two liquid paths including a first liquid path leading from the coupling portion, past the piston and into the inlet chamber or the outlet chamber, the first liquid path being closed when the piston enters the inlet side of the metering chamber from the inlet chamber and being open when the piston exits the outlet side of the metering chamber and enters the outlet chamber, and a second liquid path leading from the coupling portion, through the piston and into the metering chamber, the conveyor device further including an inlet valve disposed in the second liquid path, the inlet valve closing when there is an overpressure in the metering chamber.

11. The discharge head as claimed in claim 10, wherein the first liquid path is disposed to provide fluid communication between the coupling portion and either the inlet chamber or the outlet chamber via a first liquid path portion which extends exteriorly of the piston, and the second liquid path is disposed to provide fluid communication between the coupling portion and the metering chamber via a second liquid path portion which extends interiorly through the piston.

12. The discharge head as claimed in claim 11, wherein the cylindrical wall defines both of the inlet chamber and the outlet chamber and the metering chamber is disposed between the inlet chamber and the outlet chamber, an exterior of the piston makes sealing contact with the cylindrical wall and closes the first liquid path when the piston is disposed in the metering chamber, and the piston is not in sealing contact with the cylindrical wall and the first liquid path is open when the piston is disposed in the inlet and outlet chambers.

13. The discharge head as claimed in claim 10, wherein the cylindrical wall defines both of the inlet chamber and the outlet chamber and the metering chamber is disposed between the inlet chamber and the outlet chamber, the inlet and outlet chambers each have a cross section which is larger than a cross section of the metering chamber, an exterior of the piston makes sealing contact with the cylindrical wall and closes the first liquid path when the piston is disposed in the metering chamber, and the piston is not in sealing contact with the cylindrical wall and the first liquid path is open when the piston is disposed in the inlet and outlet chambers.

14. A discharge head for a liquid dispenser, said discharge head comprising:
   a housing including a coupling portion configured for mounting on a liquid reservoir and a discharge opening disposed to discharge liquid from said housing;
   a manually-actuable conveyor arrangement for conveying liquid from said coupling portion to said discharge opening; said conveyor arrangement comprising:
      a peripheral wall defining a metering chamber therein, said metering chamber having an outlet side disposed adjacent and in fluid communication with said discharge opening and an inlet side disposed adjacent and in fluid communication with said coupling portion;
      a piston dimensioned for slidable displacement within said metering chamber along said peripheral wall, said peripheral wall and said piston being manually displaceable relative to one another between a starting position and an ending position;
      an outlet chamber disposed adjacent and in fluid communication with said outlet side of said metering chamber and an inlet chamber disposed adjacent and in fluid communication with said inlet side of said metering chamber, a cross section of each of said inlet and outlet chambers being larger than a cross section of said piston, said piston being disposed in said inlet chamber when in the starting position and being disposed in said outlet chamber when in the ending position, said piston, during a transition from the starting position to the ending position, pressurizing liquid in said metering chamber to cause a discharge of liquid through said discharge opening;
      a first liquid path disposed to provide fluid communication between said coupling portion and said inlet chamber or said outlet chamber, said first liquid path having a portion which extends exteriorly of said piston, said piston closing said first liquid path when said piston enters said inlet side of said metering chamber from said inlet chamber and said piston opening said first liquid path when said piston exits said outlet side of said metering chamber and enters said outlet chamber;
      a second liquid path disposed to provide fluid communication between said coupling portion and said metering chamber, said second liquid path having a portion which extends interiorly through said piston; and
      an inlet valve disposed within said second liquid path, said inlet valve closing when an overpressure is present in said metering chamber.

15. The discharge head as claimed in claim 14, wherein said peripheral wall defines both said outlet chamber and said inlet chamber and said metering chamber is disposed between said inlet and outlet chambers, said piston having a cross-section similar to a cross-section of said metering chamber such that said piston makes sealing contact with said peripheral wall and closes said first liquid path when said piston is disposed in said metering chamber, both of said outlet and inlet chambers having a cross-section which is greater than the cross-section of said metering chamber and greater than the cross-section of said piston such that said piston is not in sealing contact with said peripheral wall and said first liquid path is open when said piston is disposed in said inlet and outlet chambers.

16. The discharge head as claimed in claim 14, wherein said first liquid path when open extends from said coupling portion, between an exterior of said piston and said peripheral wall and into said inlet chamber or said outlet chamber, and said second liquid path when open extends from said coupling portion, through an interior of said piston and to said metering chamber.

17. The discharge head as claimed in claim 14, wherein when said piston and said peripheral wall are manually displaced relative to one another in an actuation direction from the starting position, liquid is forced along said first liquid path in a direction towards said coupling portion, said piston closing off said first liquid path upon entering said metering chamber from said inlet chamber to cause discharge of liquid from said metering chamber and outwardly through said discharge opening.

18. The discharge head as claimed in claim 17, further including a valve disposed to open and close said discharge opening, wherein manual displacement of said piston and said peripheral wall relative to one another in the actuation direction from the starting position increases a pressure of liquid within said metering chamber to cause opening of said valve and discharge of liquid from said metering chamber and outwardly through said discharge opening.

19. The discharge head as claimed in claim 18, wherein continued manual displacement of said piston and said peripheral wall relative to one another in the actuation direction from the starting position causes said piston and said peripheral wall to reach the ending position wherein said first liquid path is opened upon said piston exiting said metering chamber and entering said outlet chamber.

20. The discharge head as claimed in claim 14, wherein said piston makes sealing contact with said peripheral wall and closes off said first liquid path only when said piston is positioned in said metering chamber, and said piston is out of sealing contact with said peripheral wall and allows opening of said first liquid path when said piston is located within said inlet and outlet chambers.

* * * * *